United States Patent [19]

Hasegawa

[11] Patent Number: 5,185,777
[45] Date of Patent: Feb. 9, 1993

[54] X-RAY RADIOGRAPHING SYSTEM WITH SPOT-FILM DEVICE

[75] Inventor: Kiyoshi Hasegawa, Tochigi, Japan

[73] Assignee: Kabushiki Kaisha Toshiba, Kanagawa, Japan

[21] Appl. No.: 661,187

[22] Filed: Feb. 27, 1991

[30] Foreign Application Priority Data

Mar. 1, 1990 [JP]  Japan .................. 2-47316

[51] Int. Cl.$^5$ ............................. G03B 42/02
[52] U.S. Cl. .................. 378/176; 378/172; 378/173; 378/177; 378/181; 250/327.2
[58] Field of Search .............. 378/172, 173, 174, 176, 378/177, 181; 250/327.2

[56] References Cited

U.S. PATENT DOCUMENTS

| | | | |
|---|---|---|---|
| 3,222,518 | 12/1965 | Nagel | 378/172 |
| 3,614,427 | 10/1971 | Vacher | 378/172 |
| 4,086,493 | 4/1978 | Krumrey et al. | 378/173 |
| 4,282,439 | 8/1981 | Matsuura | 378/173 |
| 4,365,342 | 12/1982 | Vepy | 378/173 |
| 4,365,344 | 12/1982 | Dornheim . | |
| 4,365,345 | 12/1982 | Craig . | |
| 4,433,429 | 2/1984 | Finkenzeller . | |
| 4,618,979 | 10/1986 | Koyama | 378/176 |
| 4,667,102 | 5/1987 | Koyama et al. | 378/173 |
| 4,767,113 | 8/1988 | Hasegawa et al. . | |
| 4,782,505 | 11/1988 | Ogo . | |
| 4,796,285 | 1/1989 | Sakakihara et al. . | |
| 4,802,002 | 1/1989 | Plut . | |

Primary Examiner—David P. Porta
Attorney, Agent, or Firm—Finnegan, Henderson, Farabow, Garrett and Dunner

[57] ABSTRACT

An X-ray radiographing system is provided with a table having a spot-film device which moves synchronously with an X-ray generator along a longitudinal axis (a patient's body axis) of the table. The spot-film device comprises a fluoroscopic area and a radiographic area arranged along a transverse axis at a front portion of the table. A film holder holding an X-ray sheet film (unexposed or exposed) shuttles along a transverse rail between the fluoroscopic area and a radiographic area. A feed magazine and a take-up magazine are provided under the fluoroscopic area. Unexposed X-ray sheet film is removed by suction cups from an opening in the feed magazine, and fed to the film holder. Exposed X-ray film is returned to the take-up magazine. Both the magazines can be loaded and unloaded from the front portion of the device.

23 Claims, 6 Drawing Sheets

X-RAY RADIOGRAPHING SYSTEM WITH SPOT-FILM DEVICE

BACKGROUND OF THE INVENTION

The present invention relates to an X-ray radiographing system having a spot-film device transporting an X-ray sheet film between a fluoroscopic area and a radiographing area and, in particular, to an X-ray radiographing system which enables to enlarge a longitudinal (used in the meaning of "in the direction of a body axis of a patient (an axis going through the head and toe of a patient)" hereinafter) radiographic range along a body axis of a patient.

An X-ray radiographing system disposed in a radiographing chamber is provided with an X-ray generator, and a table which includes a spot-film device inside and a tabletop on the top side on which a patient lies down. Owing to an adequate drive and holder, the X-ray generator and the spot-film device move synchronously (i.e. keeping the same position along the X-ray proceeding direction, here in this specification) and longitudinally, facing each other with the patient on the tabletop therebetween.

While a fluoroscopic area and a radiographic area between which a film holder holding an X-ray sheet film shuttles are arranged each other longitudinally inside the spot-film device, the film holder is transported for radiographing the patient from the fluoroscopic area to the radiographic area. The X-ray sheet film is exposed at the radiographic area by the X-ray which has been radiated by the X-ray generator and penetrated the patient. Normally, the X-ray radiographic system includes an image intensifier (abbreviated as "I.I." hereinafter), a television camera and an X-ray television monitor, costituting an X-ray television system.

The X-ray which has penetrated the patient enters the I.I. through the radioraphic area when the film holder is located at the fluoroscopic area. The I.I. transduces the incident X-ray to a fluorescent light and outputs this fluorescent light to the television camera. The television camera generally has a CCD (Charge Coupled Device) loaded, and the CCD transduces the incident fluorescent light to an electric video signal. The video signal generated at the CCD gets input to the X-ray television monitor. An operator of the X-ray radiographing system can observe an image of the X-ray-radiated part of the patient on a screen of the X-ray television monitor.

If the operator gets the image of the part suitable to radiograph on the screen of the X-ray television monitor, he can transport the film holder to the radiographic area and radiograph this part on the XS-ray sheet film.

The X-ray sheet films to be exposed (unexposed X-ray sheet films) are piled up and stored within a feed magazine inside the spot-film device and are fed to the film holder at the fluoroscopic area through a gap between the rubber rollers clamped each other by pulling springs, before radiographing. On the other hand, the exposed X-ray sheet films are also fed through a gap between the same rubber rollers to a take-up magazine inside the spot-film device. During this feeding process of the unexposed X-ray sheet film, a suction-cup mechanism is commonly used for feeding the unexposed X-ray sheet film from the feed magazine to the rubber rollers.

In the above-mentioned X-ray radiographing system, a large-sized X-ray picture can be taken by using an X-ray film cassette (simply called "cassette" hereinafter), if necessary. In this case, the operator who once has loaded X-ray sheet film to the film holder and operates a console for functioning this X-ray radiographing system outside the radiographing chamber, avoiding X-ray exposure, reenters the radiographing chamber and exchanges the film holder and the cassette holder holding the cassette at the spot-film device.

In the above-mentioned X-ray radiographing system, however, when an economical life-size table whose longitudinal ends coincide with the top of the head and the toe of a patient, respectively, is employed, the moving range of both the radiographic area and fluoroscopic area, which move longitudinally following the travel of the spot-film device, is contracted while these areas are supposed to cover the top of the head through the toe of the patient.

Because the spot-film device contained inside the table only travels within both of the longitudinal ends of the table, the film holder which shuttles longitudinally between both areas cannot transfer entirely to cover the top of the head through the toe of the patient. If the radiographic area covers the top of the head for example at one longitudinal end, then this radiographic area cannot cover the toe at the other longitudinal end, which are covered by the fluoroscopic area. In other words, the operator is unable to carry out the fluoroscopy and radiography concerning the toe of the patient positioned at one end of the table.

Therefore, on one hand, if the economical compact table is employed, the diagnostic range with regard to the whole-body radiography is restricted and insufficient. On the other hand, the table becomes large and costly, so as to acquire a sufficient diagnostic range regarding the whole-body radiography.

In another viewpoint, when the atmosphere surrounding X-ray sheet films piled up and stored within the feed magazine and take-up magazine becomes moist, the emulsifying agent coated on the X-ray sheet films gets sticky and causes the adjacent X-ray sheet films to adhere each other. On the contrary, the excessive dryness causes various troubles in the operation of the X-ray radiographing system. So far, a radiographing chamber has been equipped with both of a moistener and dryer in order to keep the moisture appropriate to operate the X-ray radiographing system.

The moistener and dryer, however, cannot necessarily control the moisture inside the spot-film device. Furthermore, the moistener and dryer require a water-supplier and drainage, respectively, and end up costly.

In a further viewpoint, the each opening of the feed magazine and take-up magazine contained in the spot-film device is covered by a shutter plate when unused, and opened by sliding and pushing the shutter plate out of the spot-film device when the X-ray sheet film gets pulled out and pushed in therethrough. The shutter plate pushed out of the spot-film device, however, hinders the operator from walking around the table containing the spot-film device for the operation.

In addition, the rubber rollers clamped by the pulling springs, which feed the X-ray sheet films through their gaps, are very hard to keep these gaps constant, due to the change of spring force. For this reason, the gaps of the rubber rollers come to have the different distance at the both sides. As a result, the X-ray sheet film going through these gaps happens to slip out of the due course because of the inequal friction at the both sides of the gaps, and to get loaded to the film holder inaccurately.

Lastly, the prior suction-cup mechanism mentioned before uses the horizontal chain for transferring the suction cups which have sucked the X-ray sheet film toward the rubber rollers to feed the X-ray sheet films. This horizontal chain requires considerable space inside the spot-film device, thus making the spot-film device large and uneconomical.

SUMMARY OF THE INVENTION

An object of the present invention is to substantially elliminate defects o drawbacks encountered in the prior art described above and to provide an X-ray radiographing system including a spot-film device accomplishing a substantially reduced size and a sufficient radiographic range.

Another object of the present invention is to provide an X-ray radiographing system including a spot-film device which can have both of a film holder and cassette holder loaded at the same time.

A further object of the present invention is to provide an X-ray radiographing system which does not demand any water-supplier and drainage for the moisture-controlling.

A still further object of the present invention is to provide an X-ray radiographing system including a spot-film device which does not hinders an operator from walking around the spot-film device, when a feed magazine and take-up magazine is opened.

A still further object of the present invention is to provide an X-ray radiographing system including a spot-film device where an X-ray sheet film is carried accurately.

A still further object of the present invention is to provide an X-ray radiographing system including a spot-film device provided a suction-cup mechanism which enables the spot-film device to be small and inexpensive.

These and other objects of the present invention can be achieved in one aspect by providing an X-ray radiographing system comprising a table having a tabletop for positioning a patient in a longitudinal direction of the table, an X-ray generator moving along the longitudinal direction of the table over the patient, and a spot-film device contained in the table, to be movable along the longitudinal direction of the table and synchronously with the X-ray generator, and to take a fluoroscopic area and a radiographic area arranged traversely each other, said spot-film device comprising a film containing means for containing an unexposed X-ray sheet film and an exposed X-ray sheet film, and a film carrying means for carrying an X-ray sheet film between the film containing means and the fluoroscopic areas, film feeding means for feeding an unexposed X-ray sheet film from the film containing means to the film carrying means, and a film conveying means for conveying an X-ray film between the fluoroscopic area and the radiographic area.

In preferred embodiments, an X-ray film is referred to as an X-ray sheet film and an X-ray film cassette, and there is provided a film holder holding an X-ray sheet film and rails along which the film holder shuttles between the fluoroscopic area and the radiographic area.

Further, the rail includes staged rails having portions lying on different levels along which the film holder shuttles between the fluoroscopic area and the radiographic area and in which the radiograpic area is higher than the fluoroscopic area, other than the film holder, there is provided a cassette holder holding an X-ray film cassette, and a rail along which the cassette holder slides and on which the cassette holder is positioned at the same level with the film holder at the radiographic area.

In addition, the spot-film device includes a moisture-controlling agent inside.

Besides, a feed magazine and a take-up magazine are used for storing un exposed X-ray sheet films and exposed X-ray sheet films, respectively, and these magazines are provided with a casing containing an X-ray sheet film, shutter plates covering the casing, and link mechanism, the link mechanism sliding the shutter plates over another shutter plate through the rotation.

Moreover, there is given a film carrier as the film carrying means having a rotary shaft mechanism including two shafts, support plates for supporting the two shafts in parallel each other, and a roller means attached to the two shafts, keeping a gap through which an X-ray sheet film goes keeping in touch therewith.

In the last place, there is provided a suction-cup mechanism as a film feeding means equipped with a suction-cup mechanism provided with a rotary shaft mechanism including two parallel shafts, one of which has oppositely threaded parts, and two motors rotating the two shafts, respectively, a link mechanism including two links rotatably hanged to the threaded part of the one shaft at each one end via a movable gear means and rotatably crossed each other, a suction cup means rotatably attached to the two links at each of the other end, and a fixed gear means fixed to the other shaft and geared into the movable gear means.

BRIEF DESCRIPTION OF THE DRAWINGS

For a better understanding of the present invention and to show how the same is carried out, reference is made, by way of preferred embodiments, to the accompanying drawings, in which.

DETAILED DESCRIPTION OF THE PREFERRED EMBODIMENTS

Figure 12:
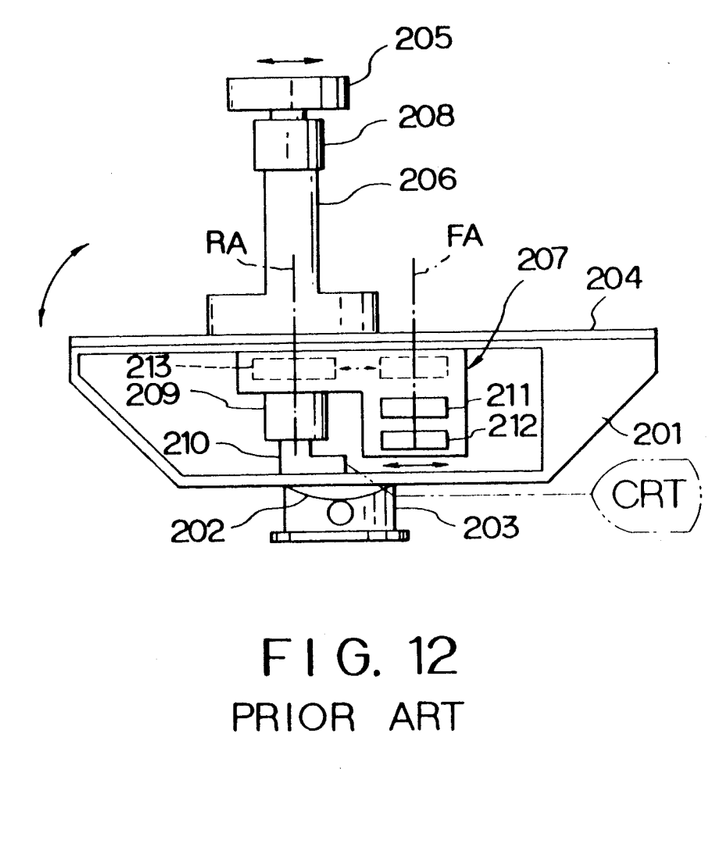
FIG. 12 is a front view of a conventional X-ray radiographing system.
Figure 13:
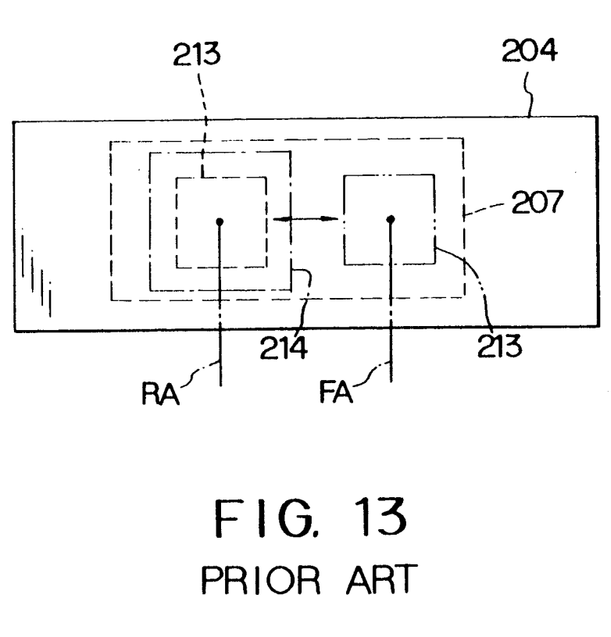
FIG. 13 is a schematic illustration of a spot-film device included in the same X-radiographing system.

In order to facilitate the understanding of the present invention, a conventional X-ray radiographing system will be described with reference to FIGS. 12 and 13. FIG. 12 is a front view of a conventional X-ray radiographing system, and FIG. 13 is a schematic illustration of a table beheld from an upper side included in the same X-ray radiographing system shown in FIG. 12.

A table 201 is attached through a rotating mechanism 202 to a base 203 tiltably. A rectangular tabletop 204 on which a patient lies down is secured at the upper side of the table 201. An X-ray generator 205 is mounted to the support pole 206 which is slidably attached to the table 201, looking down at the patient lying on the tabletop 204. The table 201 contains a spot-film device 207 inside which travels synchronously with the X-ray generator 205 by means of an unshown drive device between the longitudinal ends of the table 201.

A collimator 208 which is attached to the X-ray generator 205 in order to define the X-ray radiating area for the patient. An I.I. 209 is mounted to the spot-film device 207 on the opposite side of the patient, and a television camera 210 is neighbored with the I.I. 209. The television camera 210 is electorically connected to a television monitor CRT. The spot-film device 207 is provided with a feed magazine 211 and a take-up magazine 212 which get put into the spot-film device 207 from the front side.

The spot-film device 207 has a film holder 213 loaded that shuttles longitudinally between a fluoroscopic area FA and a radiographic area RA. An operator can convey the film holder 213 from the fluoroscopic area FA to the radiographic area RA so as to radiograph by functioning a proper drive unit (not shown). The film holder 213 comes back to the fluoroscopic area FA automatically after radiographing.

In case of a "divisional radiography" where a part of the X-ray sheet film is radiographed, the film holder 213 further moves around a field surrounded by the one dot-chain line 214 at the radiographic area RA. When the table 201 is furnished with a shoulder rest and a foot rest, this X-ray radiographing system is able to radiograph the patient at the various angle by tilting the table 201.

The X-ray generator 205 radiates an X-ray toward the patient lying on the tabletop 204. This X-ray forwards through the X-ray radiating area defined by the collimator 208 and penetrates the patient lying on the tabletop 204. When the film holder 213 holding an X-ray sheet film is placed in the fluoroscopic area FA, the X-ray having penetrated the patient goes through the radiographic area RA at the spot-film device 207 and enters the I.I. 209. The incident X-ray gets transduced to the fluorescent light inside the I.I. 209. Next, this fluorescent light gets out of the I.I. 209 and goes into the television camera 210.

An operator watches the television monitor CRT and searches the radiographic part of the patient. The operator can move the X-ray generator 205 and I.I. 209 attached to the spot-film device 207 longitudinally to obtain the part suitable to radiograph. When the operator attains the desired radiographic part, he can take an X-ray picture after conveying the film holder to the radiographic area RA.

Such a conventional X-ray radiographing system, however, has the problems mentioned hereinbefore.

Embodiments of the present invention will now be described in detail with reference to FIGS. 1 to 11, in which the components that are common to the embodiments described below will be referred to by the same reference numerals and codes. The reference numerals and codes in FIGS. 12 and 13 are reused to the members or elements shown in the following figures, which are substantially identical with those referred to by these reference numerals.

Figure 1:
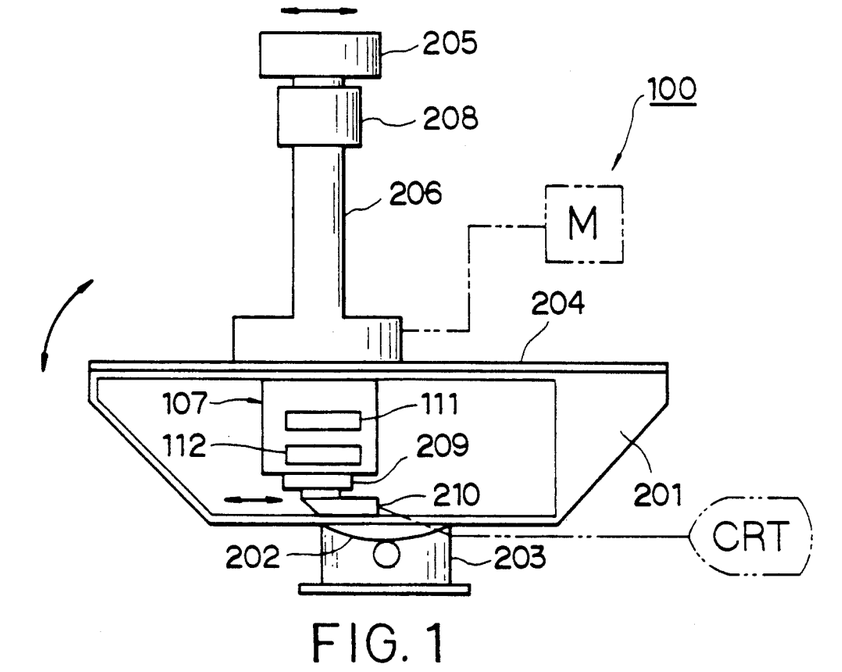
FIG. 1 is a front view of an X-ray radiographing system in accordance with a first embodiment of the present invention.
Figure 2:
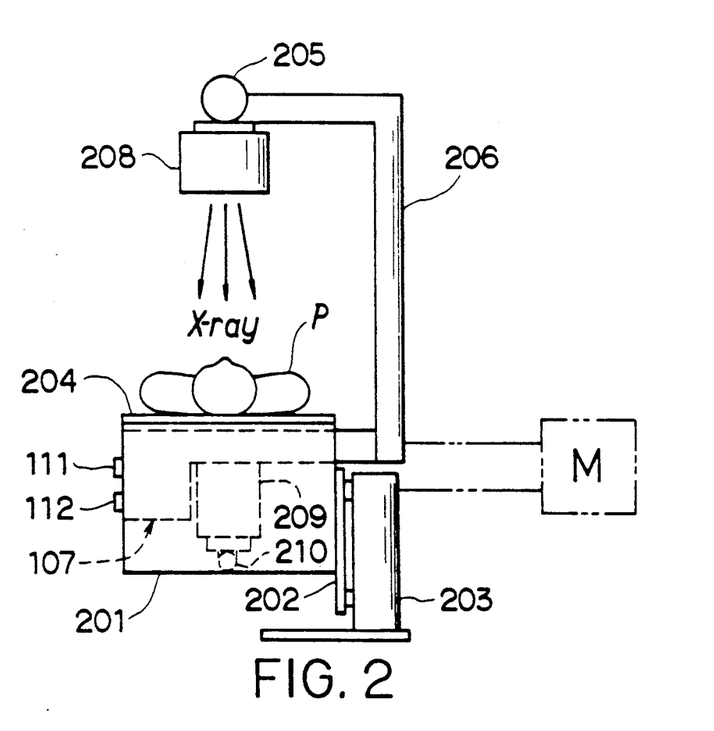
FIG. 2 is a right side view of the same X-ray radiographing system.

FIG. 1 is a front view of an X-ray radiographing system 100 in accordance with a first embodiment of the present invention. FIG. 2 is a right side view of this X-ray radiographing system 100.

The table 201 contains the spot-film device 107 attached to the support pole 206 inside which travels synchronously with the X-ray generator 205 by means of a motor M between the longitudinal ends of the table 101.

The spot-film device 107 is provided with a feed magazine 111 and take-up magazine 112 storing, respectively, unexposed X-ray sheet films and exposed X-ray sheet films, which get put into the spot-film device 107 from the front side. When the table 201 is furnished with a shoulder rest and foot rest, this X-ray radiographing system 100 is able to radiograph a patient P at the various angle by tilting the table 201 through the work of the motor M. It is also possible to use separate motors for tilting the table 201 and for sliding the support pole 206 supporting the X-ray generator 205 and the spot-film device 107.

Figure 3:
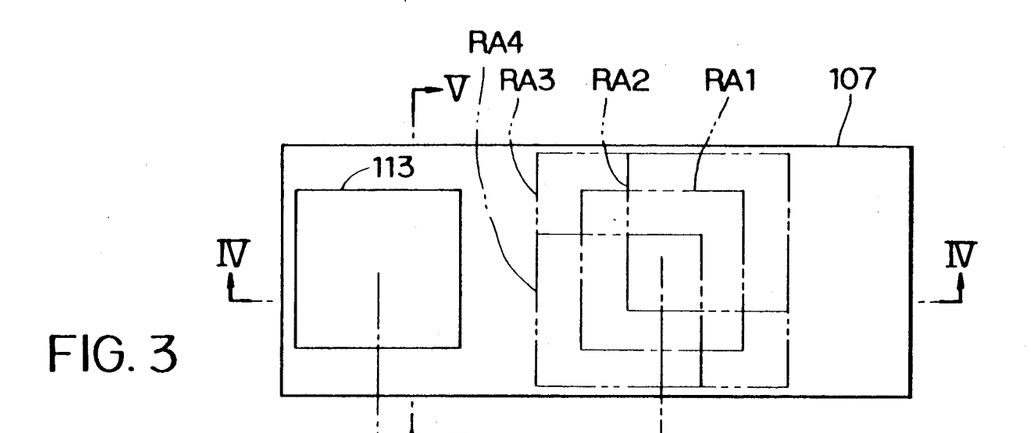
FIG. 3 is a schematic illustration of a spot-film device viewed from the upper side included in the same X-radiographing system.
Figure 4:
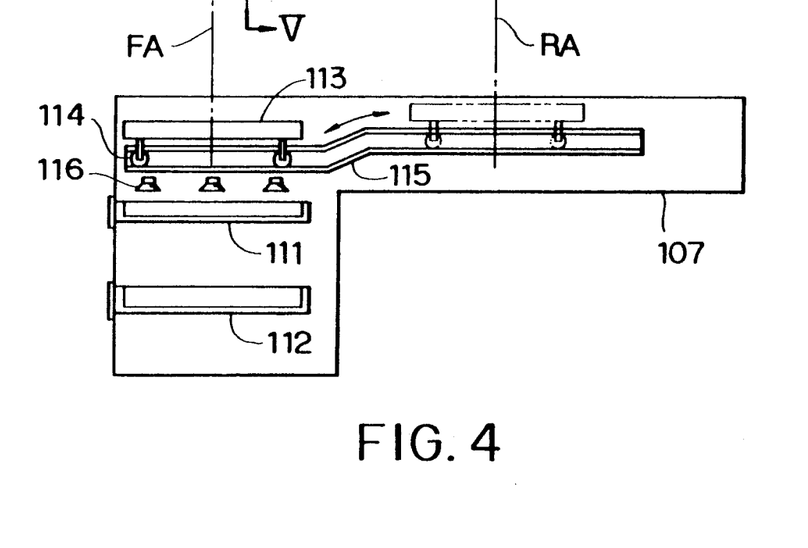
FIG. 4 is a sectional view taken along the line IV—IV of FIG. 3.
Figure 5:
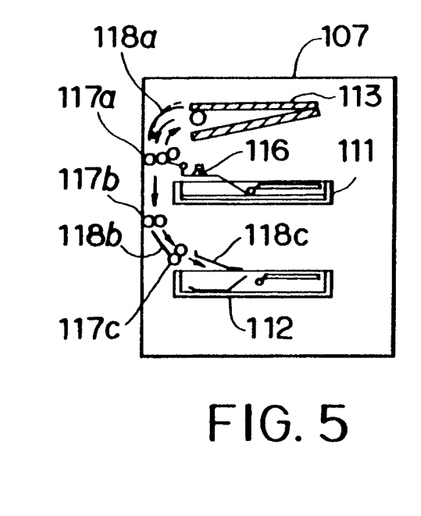
FIG. 5 is a sectional view taken along the line V—V of FIG. 3.

FIG. 3 is a schematic illustration of the spot-film device 107. FIGS. 4 and 5 are sectional views taken along the lines IV—IV and V—V, respectively, in FIG. 3. In the upper part Of the spot-film device 107, as seen from FIG. 3, a film holder 113 is conveyed between the fluoroscopic area FA and the radiographic area RA traversely (used in the meaning of "in the direction orthogonal to the body axis of the patient" hereinafter). Namely, the traverse direction and the longitudinal direction are orthogonal each other, and the traverse length of the spot-film device 107, which is equal to the traverse length of the table 101, is much shorter than the longitudinal length of the table 101.

Casters 114 attached to the film holder 113 slides by means of a film-holder drive unit (not shown) on staged rails 115 having portions lying on different levels and extending traversely. The portion at the radiographic area RA is higher (i.e. nearer to the patient P) than that at the fluoroscopic area FA with regard to the staged rails 115. Non-staged, i.e. straight, rails are able to be used for conveying the film holder 113 as well.

The operator makes the film-holder drive unit work to slide the film holder 113 to the radiographic area RA by pressing a conveyance button. The radiography is performed when the operator presses a radiography button. After the radiography is finished, the film holder 113 automatically gets back to the fluoroscopic area FA by means of the film-holder drive unit in response to a signal informing of the completion of radiography. The film holder 113 has an X-ray sheet film loaded and removed at the fluoroscopic area. The operator can effect fluoroscopy by pressing a fluoroscopy button while the film holder 113 is situated at the fluoroscopic area FA.

The unexposed X-ray sheet films piled up and stored inside the feed magazine 111 get sucked and fed by the suction cups 116 from the feed magazine 111 piece by piece. The suction cups 116 which have pulled up the unexposed X-ray sheet film feed this unexposed X-ray sheet film to a film carrier 117a. The film carrier 117a carries the unexposed X-ray sheet film to the film holder 113 at the fluoroscopic area FA.

The film holder 113 which has had the unexposed X-ray sheet film loaded conveys this unexposed X-ray sheet film to the radiographic area RA along the staged rails 115, when the radiography is performed.

The reference code RA1 specifically denotes the radiograpic area for a "whole radiography" where the whole surface of an X-ray sheet film is exposed. If the operator wishes to carry out a "divisional radiography" where an X-ray sheet film is divided into some parts and exposed part by part, the film holder 113 gets transferred to divisional radiograpic areas, RA2, RA3, and RA4, respectively, for example, every time of radiographing.

The exposed X-ray sheet film is carried through the film carriers 117a, 117b, and 117c, in this order, to the take-up magazine 112. The reference numericals 118a, 118b, and 118c are guide plates for facilitating the carrying of the X-ray sheet film.

In this embodiment, the film holder 113 both at the fluoroscopic area FA and radioscopic area RA can travel longitudinally, accompanying the longitudinal movement of the spot-film device 107, up to the very ends of the life-size table 201, because the film holder 113 shuttles traversely between the fluoroscopic area FA and radioscopic area RA. Therefore, even though the compact and economical table is employed, this X-ray radiographing system 100 enables the radiography and fluoroscopy covering from the top of the head to the toe of the patient. This X-ray radiographing system ensures both of the sufficient diagnostic range for a patient and small size.

Figure 6:
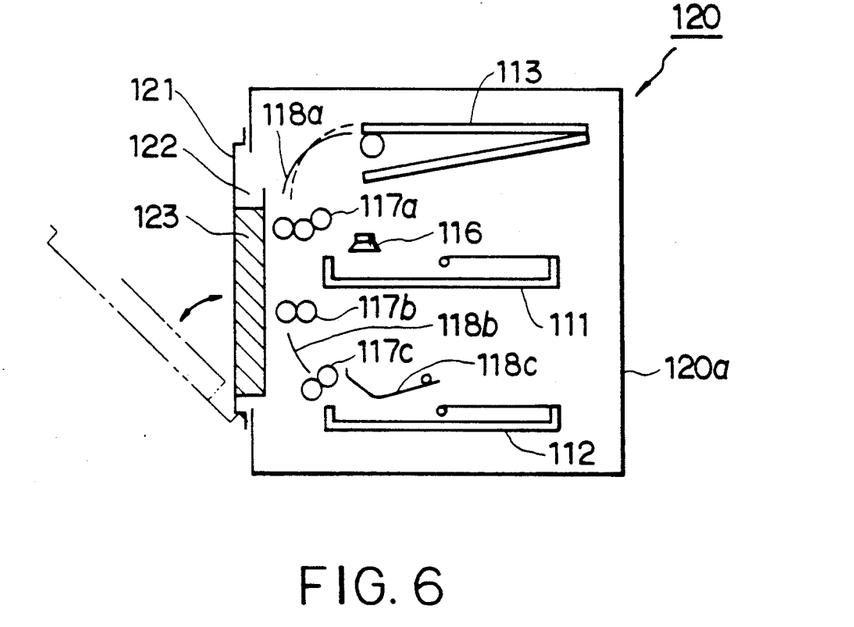
FIG. 6 is a schematic illustration of a spot-film device in accordance with a second embodiment of the present invention.

FIG. 6 is a front perspective view of a spot-film 120 in accordance with a second embodiment of the present invention.

A container 121 is mounted detachably to a hole 122 formed on the left side of an outer case 120a of the spot-film device 120. The container 121 contains a granular moisture-controlling agent 122.

The moisture-controlling agent 123 absorbs and discharges the vapor inside the spot film device 120, keeping the moisture inside the spot-film device 120 precisely at a desired level where X-ray sheet films piled up and stored within the feed magazine 111 and take-up magazine 112 never get sticky and adhere each other.

Moreover, since the moisture-controlling agent 123 does not need any water-supplier or drainage, the spot-film device 107 can be produced compactly and cheaply. The time and labor to manage the water-supplying and draining become unnecessary as well. The moisture-controlling agent 123 can be easily disposed and renewed by detaching the container 121.

The container 121 can be mounted anywhere inside the spot-film device 120, within the feed magazine 111 and take-up magazine 112, etc. Further, any kind of moisture-controlling agent can be used.

Figure 7:
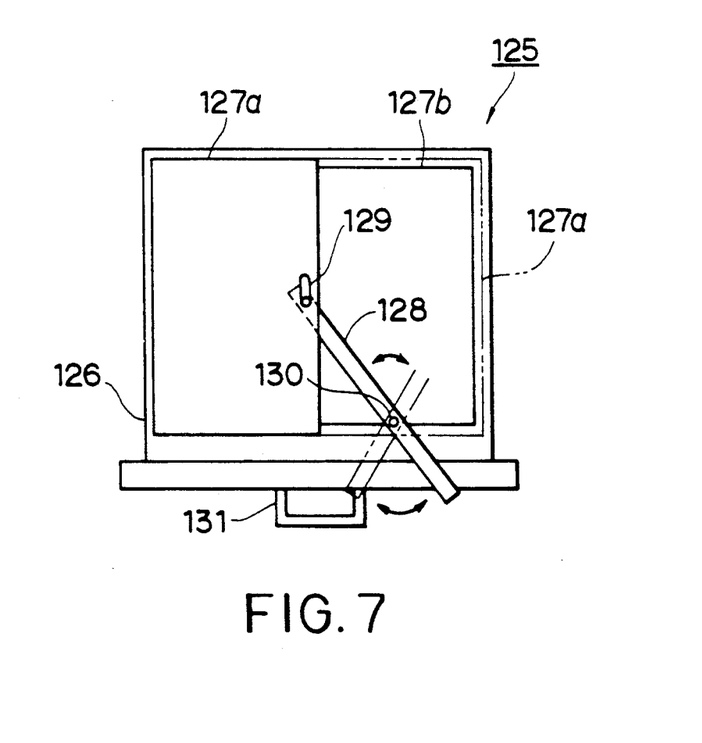
FIG. 7 is an upper view of a feed magazine in accordance with a third embodiment of the present invention.

FIG. 7 is an upper view of a feed magazine 125 in accordance with a third embodiment of the present invention.

The feed magazine 125 is equipped with a casing 126 within which unexposed X-ray sheet films are stored and two shutter plates 127a and 127b. The shutter plates 127a and 127b cover the casing 126 half and half, respectively. The shutter plate 127a, which has a link 128 hooked to a hole 129 of the shutter plate 127a, slides over the other shutter plate 127b through the rotation of the link 128. The link 128 rotates around a pin 130 by way of an unshown rotary drive mechanism. A reference numerical 131 indicates the handle attached to the casing 126 with which an operator pushes the feed magazine 125 into the spot-film device 107 and pulls the feed magazine 125 out of the spot-film device 107 at a front side of the spot-film device 107.

When the unexposed X-ray sheet film gets taken out of the feed magazine 125, the shutter plate 127a slides over the shutter plate 127b and opens the entrance through which the unexposed X-ray sheet film gets pulled out. Since neither shutter plate 127a nor 127b gets out of the spot-film device 107, extending over the casing 126, these shutter plates 127a and 127b do not hinder the operator from walking around the table 201. Needless to say, this opening mechanism using a plurality of the shutter plates 127a, 127b explained in this embodiment is applicable to the take-up magazine 112.

Figure 8:
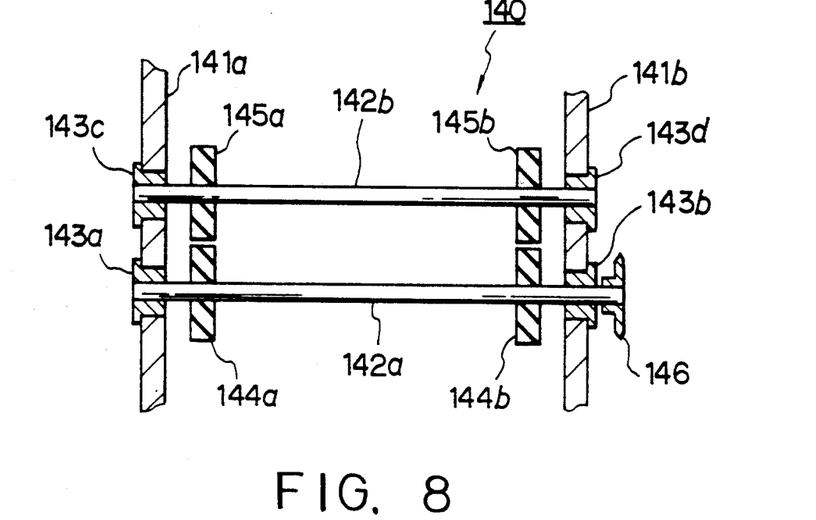
FIG. 8 is a sectional view of a film carrier in accordance with a fourth embodiment of the present invention.

FIG. 8 is a sectional view of a film carrier 140 in accordance with a fourth embodiment of the present invention. The film carrier 140 carries an unexposed X-ray sheet film from the feed magazine 111 to the film holder 113 and an exposed X-ray sheet film from the film holder 113 to the take-up magazine 112.

The film carrier 140 is provided with support plates 141a, 141b which support shafts 142a, 142b in parallel therebetween through radial bearings 143a 143b, 143c and 143d. The radial bearings 143a 143b, 143c and 143d are attached to holes located accurately on the support plates 141a and 141b to keep the shafts 142a and 142b strictly parallel with each other. Both of rubber drive rollers 144a and 144b are fixed to the shaft 141a. Each of rubber driven rollers 145a and 145b are fixed to the shaft 142b opposite to the drive rollers 144a and 144b, respectively. The shaft 142a is coupled to the adequate transmission mechanism like a sprocket or pulley, for example. If the X-ray sheet film is 0.2 mm thick, the width of a gap between the drive rollers 144a, 144b and the driven rollers 145a, 145b is preferably 0.1 mm or less narrower than the thickness of the X-ray sheet film.

The operator can operate a console outside a radiographing chamber to work the above-mentioned transmission mechanism. When the transmission mechanism works, the shaft 142a and the drive rollers 144a, 144b begin to rotate. The X-ray sheet film gets inserted to the gap between the drive rollers 144a, 144b and the driven rollers 145a, 145b by pressing these elastic rubber rollers and enlarging this gap.

The X-ray sheet film inserted to the gap between the drive rollers 144a, 144b and the driven rollers 145a, 145b get fed by means of the friction with the frictional rubber rollers 144a, 144b, 145a and 145b, accompanying the rotation of these rollers 144a. 144b, 145a and 145b.

Conventionally, since the opposite drive rollers and driven rollers have been supported each other by the pulling springs hooked thereto, the distance of the gap between the drive rollers and driven rollers is susceptible to fluctuate by the change of the pulling force of the springs. The X-ray sheet films sometimes have not progressed straight and smooth because of the unequal friction, and have caused trouble. The film carrier 140 of this embodiment, however, keeps the gap between rollers 144a, 144b, 145a and 145b strictly equal and constant since the support plates 141a and 141b are accurately molded in order to position the holes precisely to which the parallel shafts 142a and 142b are inserted. Accordingly, the film carrier 140 can carry the X-ray sheet film smoothly and accurately up to the film holder 113 and take-up magazine 112.

The drive roller and driven roller can be made of any material besides rubber so long as it is frictional and elastic. The conveyor belts which run facing each other can be employed instead of the drive and driven rollers, to the extent that their gaps are kept constant.

Figure 9:
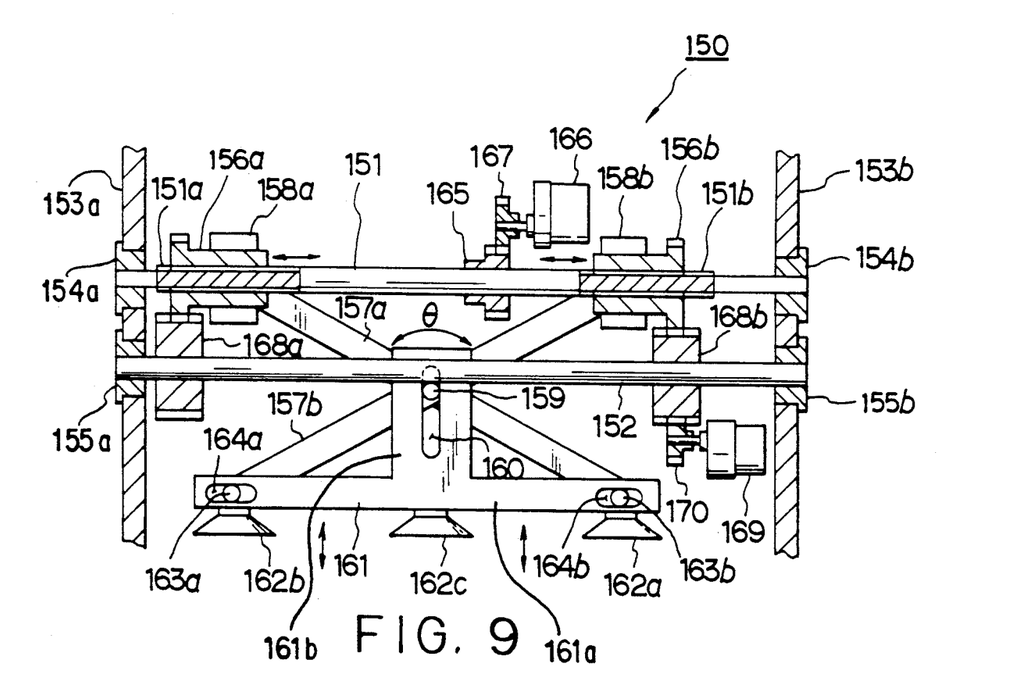
FIG. 9 is a schematic illustration of a suction-cup mechanism in accordance with a fifth embodiment of the present invention.

FIG. 9 is a schematic illustration of a suction-cup mechanism 150 of a fifth embodiment of the present invention. In order to facilitate the explanation, a sucking mechanism including a vacuum pump, hoses, etc. which connects to a suction cup is left out.

In this suction-cup mechanism 150, shafts 151, 152 are supported in parallel by support plates 153a 153b which support the feed magazine 109 as well. The shaft 151 is inserted to radial bearings 154a and 154b mounted to a hole of the support plates 153a, 153b. The shaft 152 is inserted to radial bearings 155c and 155d in the same manner. The shaft 151 has a right-thread part 151a and a left-thread part 151b in its right end part and left end part, respectively.

A right-threaded movable gear 156a and a left-threaded movable gear 156b are geared into the right-thread part 151a and the left-thread part 151b of the shaft 151. Upper ends of links 157a and 157b are rotatably coupled to couplers 158a and 158b, resectively, which are secured to the movable gears 156a and 156b, respectively. The links 157a and 157b are rotatably crossed through a pin 159 which slides vertically along a slit 160 formed at the upper part of an inverted-T-shaped suction-cup holder 161.

Suction cups 162a and 162b are mounted to lower ends of the links 157a and 157b, respectively, through pins 163a and 163b. The pins 163a and 163b slide horizontally along slits 164a and 164b, respectively, formed at both horizontal ends of the suction-cup holder 161. The links 157a, 157b hang the suction-cup holder 161 by means of the pins 163a, 163b as well. The suction cup holder 161 is provided with a third suction cup 162c at its central horizontal part.

A fixed gear 165 is fixed to the shaft 151 between the right-threaded part 151a and left-threaded part 151b. An encode motor 166 is coupled to the fixed gear 165 through a coupling gear 167. The right-threaded movable gear 156a and left-threaded movable gear 156b are geared into fixed gears 168a and 168b, respectively, which are fixed to the shaft 152. An encode motor 169 is coupled to the fixed gear 168b through a coupling gear 170.

When an operator pulls up the unexposed X-ray film from the feed magazine 109, the operator functions the motor 166 to the predetermined rotating direction and to the extent predetermined by the encoder. The work of the motor 166 gets transmitted to the shaft 151 through the coupling gear 167 and the fixed gear 165 and makes the shaft 151 rotate. The right-threaded gear 156a and left-threaded gear 156b start to move apart each other, corresponding to the rotation of the right-threaded part 151a and left-threaded part 151b of the shaft 151 in this case.

The right-threaded gear 156a and left-threaded gear 156b, however, can move only to the extent of the backlash, because these gears 156a, 156b are geared into the fixed gears 168a, 168b, respectively. Hence, the links 157a, 157b enlarge the crossing angle θ through lifting the pin 159 along the slit 160 and lift the suction-cup holder 161 and the suction cups 162a-162c sucking an unexposed sheet film vertically up to the level corresponding to the moving distance of the gears 156a, 156b. Meanwhile, the suction cups 162a and 162b keep their distance unchanged and do not lean toward any side, because these suction cups 162a, 162b rotate around the pin 163a 163b and move horizontally in accordance with the slide of the pins 163a 163b along the slits 164a, 164b.

When the pullup of the suction cups 162a-162c has been completed, the encode motor 169 works. The drive of the motor 169 makes the fixed gears 168a, 168b rotate with the shaft 152, through the coupling gear 170. If the fixed gears 168a, 168b rotate, then the fixed gears 156a, 156b geared into this fixed gears 168a, 168b rotate around the shaft 151. Thus, the suction cups 162a-162c rotate around the shaft 151, through the rotation of the couplers 158a, 158b, the links 157a, 157b and the suction-cup holder 161, and feed the unexposed X-ray sheet film to the film carrier 117a. After the feeding of the unexposed X-ray sheet film is completed, the suction cups 162a-162c are made to get back to the original position, stepping reversely. The work of the encode motors 166, 169 is controlled by the encode pulse singnal sent from the console.

So far, the suction-cup mechanism has required three encode motors for rotating the shaft connected to the links hanging the suction cups (corresponding to the shaft 151 shown) and declining the suction cups down to the X-ray sheet film stored within the feed magazine, for pulling up the suction cups vertically by rotating the chain hanging the suction cup, and for shifting the suction cups horizontally by rotating the chain hanging the suction cups. In this conventional suction-cup mechanism, the chains for shifting the suction cups vertically and horizontally demand the considerable space inside the spot-film device. For these reasons, The spot-film device including the conventional suction-cup mechanism has been large and expensive. On the contrary, the spot-film device employing the suction-cup mechanism 150 can be manufactured compactly and at low cost, because the suction-cup mechanism 150 demands only two encode motors and no chains for shifting the suction cups vertically and horizontally.

Figure 10:
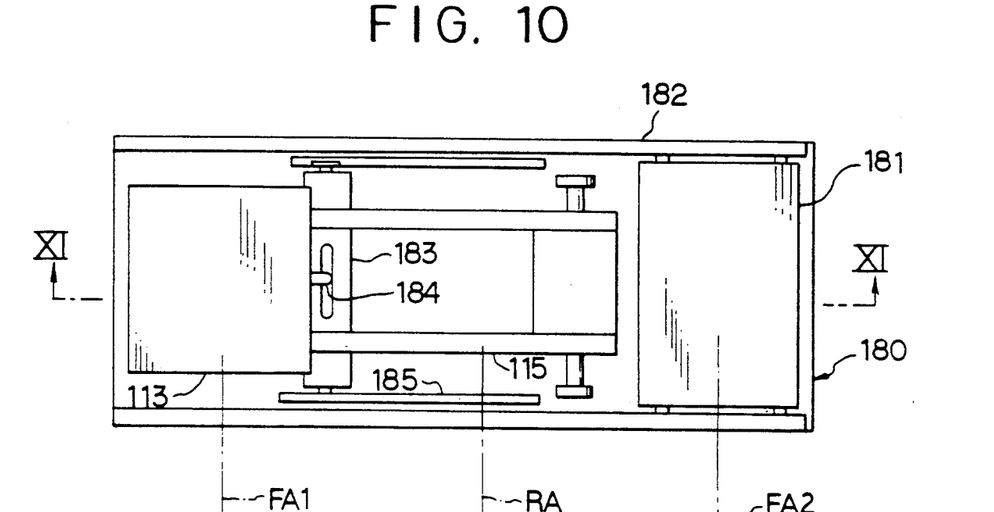
FIG. 10 is a schematic illustration of a spot-film device in accordance with a sixth embodiment of the present invention.
Figure 11:
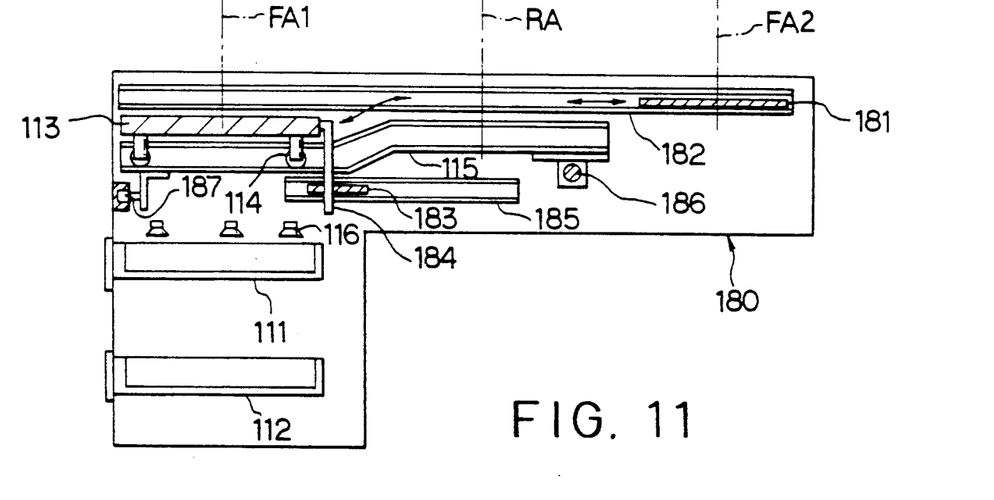
FIG. 11 is a sectional view taken along the line XI—XI of FIG. 10.

FIG. 10 is a schematic illustration of a spot-film device 180 viewed from the upper side in accordance with a sixth embodiment of this invention. FIG. 11 is a sectional view taken along the line XI—XI of FIG. 10.

When the operator is willing to radiograph the whole abdominal of a patient, a cassette which has a large-size X-ray film loaded is necessary, because an ordinary X-ray sheet film of 25.4 cm×25.4 cm, for example are too small for radiographing.

The spot-film device 180 is furnished with a cassette holder 181 holding a cassette and guide rails 182 along which the cassette holder 181 slides. The film holder 113 slides with the casters 114 along the staged rails 115, as a moving-aid piece 183 which is connected to the film holder 113 through a coppling pin 184 moves along the guide rails 185. An operator makes the moving-aid piece 183 transfer through an unshown drive unit.

The staged rails 182 slides, vertically against the drawing paper, along a guide shaft 186 through the rotation of a roller 187. The control of the displacement of the staged rail 182 and the film holder 113 at the radiographic area RA enables the afore-mentioned divisional radiography. On one hand, the film holder 113 shuttles between the fluoroscopic area FA1 and the radiographic area RA. On the other hand, the cassette holder 181 shuttles between the fluoroscopic area FA2 and the radiographic area RA.

The cassette holder 181 is transferred to the fluoroscopic area FA1 through an unshown drive unit after getting loaded. The operator makes the cassette holder 181 proceed to the radiographic area RA by pressing a conveyance button and expose the X-ray film cassette by pressing a radiography button. The cassette holder 181 gets back to th fluoroscopic area FA2 automatically after radiographing.

In this embodiment, the film holder 113 and the cassette holder 181 take the same level at the radiographic area RA so as to prevent either of their magnification ratios from changing. The spot-film device 180 can have the cassette holder 181 and the film holder 113 loaded at the same time, because owing to the staged rails 115 the cassette holder 181 and the film holder 113 do not collide with each other during proceedeing to the radiographic area RA. For this reason, it is unnecessary for the operator to reenter the radiographing chamber for exchanging the cassette holder 181 and the film holder 113. This spot-film device 180 enables the convenience of the operator and the speed-up of the radiography.

It is to be understood that the present invention is not limited to the described preferred embodiments and many other changes and modifications may be made according to the present invention without departing from the scopes of the appended claims.

What is claimed is:

1. An X-ray radiographing system comprising:
    a table having a tabletop for positioning a patient along a longitudinal axis and a front disposed a distance from the longitudinal axis along a transverse axis;
    X-ray generating means adapted to be movable along the longitudinal axis over the patient for generating X-rays directed at a radiographic area;
    a spot-film device within the table and adapted to be synchronously movable along the longitudinal axis with the X-ray generator, comprising;
        a top portion including a fluoroscopic area arranged along the transverse axis and the radiographic area,
        a front portion forming a part of the front of the table, the fluoroscopic area being disposed proximate the front portion and the radiographic area being disposed proximate the longitudinal axis,
        film containing means including;
            a feed magazine storing unexposed X-ray sheet films and having an opening through which unexposed X-ray sheet films are removed, and
            a take-up magazine storing exposed X-ray sheet films,
            said feed magazine and take-up magazine being disposed under the fluoroscopic area, being adapted to be loaded and unloaded through the front portion, and being respectively provided with a plurality of shutter plates and a link mechanism connected to one shutter plate, such that the link mechanism is rotatable to slide the one shutter plate over another shutter plate;
    film carrying means for removing unexposed X-ray sheet films from the feed magazine through the opening and carrying the unexposed X-ray sheet film to the fluoroscopic area, and for carrying exposed X-ray sheet films from the fluoroscopic area to the take-up magazine; and
    film conveying means for conveying the unexposed X-ray sheet films to the fluoroscopic area and the exposed X-ray sheet films to the radiographic area.

2. The X-ray radiographing system according to claim 1, further comprising;
    an image intensifier transducing incident X-rays radiated from the X-ray generator into fluorescent light,
    a television camera transducing the fluorescent light into an electrical video signal, and
    a television monitor displaying an X-ray image in accordance with the electrical video signal.

3. The X-ray radiographing system according to claim 1, wherein the film conveying means includes;
    film holder means for holding unexposed and exposed X-ray sheet films, and
    rail means along which the film holder means shuttles between the fluoroscopic area and the radiographic area.

4. The X-ray radiographing system according to claim 3, wherein the radiographic area comprises a plurality of divisional radiographic areas, wherein the X-ray generating means is adapted to selectively radiate each divisional radiographic area 5. An X-ray radiographing system comprising:
    a table having a tabletop for positioning a patient along a longitudinal axis and a front disposed a distance from the longitudinal axis along a transverse axis;
    X-ray generating means adapted to be movable along the longitudinal axis over the patient for generating X-rays directed at a radiographic area;
    a spot-film device within the table and adapted to be synchronously movable along the longitudinal axis with the X-ray generator, including;
        a top portion including a fluoroscopic area arranged along the transverse axis and the radiographic area, and
        a front portion forming a part of the front of the table, the fluoroscopic area being disposed proximate the front portion and the radiographic area being disposed proximate the longitudinal axis;
    film containing means including;
        a feed magazine storing unexposed X-ray sheet films and having an opening through which unexposed X-ray sheet films are removed, and
        a take-up magazine storing exposed X-ray sheet films,
        wherein the feed magazine and take-up magazine are disposed under the fluoroscopic area, and are adapted to be loaded and unloaded through the front of the table;
    film carrying means for removing unexposed X-ray sheet films from the feed magazine through the opening and carrying the unexposed X-ray sheet film to the fluoroscopic area, and for carrying exposed X-ray sheet films from the fluoroscopic area to the take-up magazine; and
    film conveying means for conveying the unexposed X-ray sheet films to the fluoroscopic area and for conveying the exposed X-ray sheet films to the radiographic area, said film conveying means including;
        film holder means for holding unexposed and exposed X-ray sheet films, a staged rail element having a plurality of rail portions, each rail portion respectively lying on a different vertical level along which the film holder means shuttles between the fluoroscopic area and the radiographic area, cassette holder means for holding an X-ray film cassette, and a rail element along which the cassette holder means slides and on which the cassette holder means is positioned at the same level as the film holder means in the radiographic area.

6. The X-ray radiographing system according to claim 5, wherein the radiographic area comprises a plurality of divisional radiographic areas, wherein the X-ray generating means selectively radiates each divisional radiographic area, and wherein the staged rail element comprises staged rails having a roller and a guide rail which facilitate sliding of the staged rail element in along the transverse and the longitudinal axes.

7. The X-ray radiographing system according to claim 6, wherein the spot-film device includes a moisture-controlling agent.

8. The X-ray radiographing system according to claim 7, wherein the spot-film device includes a detachable outer case, and a container attached inside the outer case containing the moisture-controlling agent.

9. The X-ray radiographing system according to claim 5, further comprising;

an image intensifier transducing incident X-rays radiated from the X-ray generator into fluorescent light, a television camera transducing the fluorescent light into an electrical video signal, and a television monitor displaying an X-ray image in accordance with the electrical video signal.

10. The X-ray radiographing system according to claim 5, wherein the radiographic area comprises a plurality of divisional radiographic areas, wherein the X-ray generating means is adapted to selectively radiate each divisional radiographic area.

11. An X-ray radiographing system comprising:

a table having a tabletop for positioning a patient along a longitudinal axis and a front disposed a distance from the longitudinal axis along a transverse axis;

X-ray generating means adapted to be movable along the longitudinal axis over the patient for generating X-rays directed at a radiographic area;

a spot-film device within the table and adapted to be synchronously movable along the longitudinal axis with the X-ray generator, comprising;

a top portion including a fluoroscopic area arranged along the transverse axis and the radiographic area, a front portion forming a part of the front of the table, the fluoroscopic area being disposed proximate the front portion and the radiographic area being disposed proximate the longitudinal axis, film containing means including;

a feed magazine storing unexposed X-ray sheet films and having an opening through which unexposed X-ray sheet films are removed, and a take-up magazine storing exposed X-ray sheet films, wherein the feed magazine and take-up magazine are disposed under the fluoroscopic area, and are adapted to be loaded and unloaded through the front portion;

a reversed-path film carrying mechanism for removing unexposed X-ray sheet film from the feed magazine through the opening and carrying the unexposed X-ray sheet film to the fluoroscopic area, and for carrying exposed X-ray sheet films from the fluoroscopic area to the take-up magazine, said reverse-path film carrying mechanism including;

first and second shafts extending along the transverse axis of the table, support plates supporting the first and second shafts in parallel, first pair of rollers attached to the first shaft, and second pair of rollers attached to the second shaft, wherein the first and second pairs of rollers oppose each other across a gap through which the exposed and unexposed X-ray sheet films pass, and;

film conveying means for conveying the unexposed X-ray sheet films to the fluoroscopic area and the exposed X-ray sheet films to the radiographic area.

12. The X-ray radiographing system according to claim 11, wherein at least one of said first and second pair of rollers comprises a drive roller.

13. The X-ray radiographing system according to claim 12, wherein the first and second pair of rollers are made of rubber.

14. An X-ray radiographing system comprising:

a able having a tabletop for positioning a patient along a longitudinal axis and a front disposed a distance from the longitudinal axis along a transverse axis;

X-ray generating means adapted to be movable along the longitudinal axis over the patient for generating X-rays directed at a radiographic area;

a spot-film device within the table and adapted to be synchronously movable along the longitudinal axis with the X-ray generator, comprising;

a top portion including the radiographic area and a fluoroscopic area arranged along the transverse axis, a front portion forming a part of the front of the table, the fluoroscopic area being disposed proximate the front portion and the radiographic area being disposed proximate the longitudinal axis, film containing means including;

a feed magazine storing unexposed X-ray sheet films and having an opening through which unexposed X-ray sheet films are removed, and a take-up magazine storing exposed X-ray sheet films, wherein the feed magazine and take-up magazine are disposed under the fluoroscopic area, and are adapted to be loaded and unloaded through the front portion;

film carrying means for removing unexposed X-ray sheet films from the feed magazine through the opening and carrying the unexposed X-ray sheet film to the fluoroscopic area, and for carrying exposed X-ray sheet films from the fluoroscopic area to the take-up magazine, said film carrying means including;

at least one suction-cup for grasping the unexposed X-ray sheet film, a suction-cup supporting element for supporting the suction-cups, and a suction-cup moving element for moving the suction-cup supporting element in a vertical direction, and film conveying means for conveying the unexposed and exposed X-ray sheet films between the fluoroscopic area and radiographic area.

15. The X-ray radiographing system according to claim 14, wherein the suction-cup moving element comprises:
a first shaft supported along the transverse axis of the table having oppositely threaded portions separated along the shaft by a predetermined distance;
first and second movable gears, each gear respectively meshed with one of the threaded portions of the first shaft;
a first driving member for rotating the first shaft; and
a second driving member for rotating the two movable gears;
first crossed link member coupled to the first gear and to a first end of the suction-cup supporting element;
second crossed link member coupled to the second gear and to a second end of the suction-cup supporting element;
wherein upon rotation of the first shaft the first and second crossed links change angular position relative to each other to produce vertical movement of the suction-cup supporting element.

16. The X-ray radiographing system according to claim 15, wherein the first driving member includes a gear fixed to the first shaft, and a first motor driving the first fixed gear with a first coupling gear; and
wherein said second driving member includes a second shaft supported in parallel with the first shaft, third and fourth gears fixed to the second shaft, respectively meshed with one of the two movable gears, and a second motor driving at least one of the third and fourth fixed gears with a second coupling gear.

17. The X-ray radiographing system according to claim 15, wherein the suction-cup supporting element comprises an inverted T-shape member having a base extending along the transverse axis of the table and a pillar member at a central position of the base.

18. The X-ray radiographing system according to claim 17, wherein the first crossed link member includes a pin upon which the first and second crossed link members rotate, and
wherein the pillar member of the suction-cup supporting element includes a vertical slot portion formed in a central portion of the pillar, wherein the pin is slidably coupled in the slot.

19. The X-ray radiographing system according to claim 17, wherein the first crossed link member includes a first pin slidably coupled to a first slot in the first end of the suction-cup supporting element; and
wherein the second crossed link member includes a second pin slidably coupled to a second slot in the second end of the suction-cup supporting element.

20. The X-ray radiographing system according to claim 17, wherein the suction-cups include at least two suction-cups respectively attached to one of the end portions of the base.

21. The X-ray radiographing system according to claim 14, further comprising;
an image intensifier transducing incident X-rays radiated from the X-ray generator into fluorescent light,
a television camera transducing the fluorescent light into an electrical video signal, and
a television monitor displaying an X-ray image in accordance with the electrical video signal.

22. The X-ray radiographing system according to claim 14, wherein the film conveying means includes;
film holder means for holding unexposed and exposed X-ray sheet films, and
rail means along which the film holder means shuttles between the fluoroscopic area and the radiographic area.

23. The X-ray radiographing system according to claim 22, wherein the radiographic area comprises a plurality of divisional radiographic areas, wherein the X-ray generating means is adapted to selectively radiate each divisional radiographic area.

* * * * *

UNITED STATES PATENT AND TRADEMARK OFFICE
CERTIFICATE OF CORRECTION

PATENT NO. : 5,185,777
DATED : February 09, 1993
INVENTOR(S) : Kiyoshi Hasegawa

It is certified that error appears in the above-indentified patent and that said Letters Patent is hereby corrected as shown below:

Claim 14, column 14, line 28, change "able" to --table--.

Signed and Sealed this

Eleventh Day of January, 1994

*Attest:*

BRUCE LEHMAN

*Attesting Officer*  *Commissioner of Patents and Trademarks*